(12) United States Patent
Nakao et al.

(10) Patent No.: US 9,841,384 B2
(45) Date of Patent: Dec. 12, 2017

(54) DEFECT INSPECTING METHOD AND DEFECT INSPECTING APPARATUS

(71) Applicant: HITACHI HIGH-TECHNOLOGIES CORPORATION, Tokyo (JP)

(72) Inventors: Toshiyuki Nakao, Yokohama (JP); Shigenobu Maruyama, Oiso (JP); Akira Hamamatsu, Yokohama (JP); Yuta Urano, Yokohama (JP)

(73) Assignee: HITACHI HIGH-TECHNOLOGIES CORPORATION, Tokyo (JP)

( * ) Notice: Subject to any disclaimer, the term of this patent is extended or adjusted under 35 U.S.C. 154(b) by 94 days.

(21) Appl. No.: 14/986,824

(22) Filed: Jan. 4, 2016

(65) Prior Publication Data

US 2016/0116421 A1 Apr. 28, 2016

Related U.S. Application Data

(63) Continuation of application No. 14/154,612, filed on Jan. 14, 2014, now Pat. No. 9,228,960, which is a (Continued)

(30) Foreign Application Priority Data

Feb. 27, 2009 (JP) .................................. 2009-045857

(51) Int. Cl.
*G01N 21/00* (2006.01)
*G01N 21/95* (2006.01)
(Continued)

(52) U.S. Cl.
CPC ..... *G01N 21/9501* (2013.01); *G01N 21/8806* (2013.01); *H01L 22/12* (2013.01);
(Continued)

(58) Field of Classification Search
CPC ...................................................... G01N 21/00
(Continued)

(56) References Cited

U.S. PATENT DOCUMENTS

| 5,486,919 A | * | 1/1996 | Tsuji | ...................... | G01N 21/88 356/237.4 |
| 5,903,342 A | * | 5/1999 | Yatsugake | .............. | G01N 21/94 250/559.41 |

(Continued)

FOREIGN PATENT DOCUMENTS

| JP | 09-304289 | 11/1997 |
| JP | 11-258175 | 9/1999 |

(Continued)

OTHER PUBLICATIONS

Andy Steinbach et al., Generating High-Speed, Full-water Maps of Surface Microroughness, Yield Management Solutions, Dec. 2006.

*Primary Examiner* — Roy M Punnoose
(74) *Attorney, Agent, or Firm* — Baker Botts L.L.P.

(57) ABSTRACT

A defect inspecting method and apparatus for inspecting a surface state including a defect on a wafer surface, in which a polarization state of a laser beam irradiated onto the wafer surface is connected into a specified polarization state, the converted laser beam having the specified polarization state is inserted onto the wafer surface, and a scattering light occurring from an irradiated region where the laser beam having the specified polarization state is irradiated, is separated into a first scattering light occurring due to a defect on the wafer and a second scattering light occurring due to a surface roughness on the wafer. An optical element for optical path division separates the first and second scattering lights approximately at the same time.

19 Claims, 11 Drawing Sheets

Related U.S. Application Data continuation of application No. 13/146,428, filed as application No. PCT/JP2009/006887 on Dec. 15, 2009, now Pat. No. 8,638,429.

(51) Int. Cl.
   *G01N 21/88* (2006.01)
   *H01L 21/66* (2006.01)

(52) U.S. Cl.
   CPC ............ *G01N 2021/8809* (2013.01); *G01N 2021/8848* (2013.01)

(58) Field of Classification Search
   USPC ........................... 356/237.2, 364, 369
   See application file for complete search history.

(56) References Cited

U.S. PATENT DOCUMENTS

| | | | |
|---|---|---|---|
| 6,034,776 A | 3/2000 | Germer et al. | |
| 7,075,630 B2* | 7/2006 | Meeks | G01B 11/0616 257/E21.53 |
| 7,110,106 B2* | 9/2006 | Xu | G01N 21/474 356/237.1 |
| 7,161,671 B2* | 1/2007 | Shibata | G01N 21/95607 250/559.42 |
| 7,433,031 B2* | 10/2008 | Xu | G01N 21/21 356/237.2 |
| 7,623,227 B2* | 11/2009 | Judell | G01N 21/21 356/237.2 |
| 7,710,557 B2* | 5/2010 | Oshima | G01N 21/9501 250/559.45 |
| 7,714,997 B2* | 5/2010 | Shibata | G01N 21/21 356/237.2 |
| 7,719,673 B2 | 5/2010 | Oshima et al. | |
| 8,004,666 B2* | 8/2011 | Shibata | G01N 21/21 356/237.1 |
| 8,035,808 B2* | 10/2011 | Oshima | G01N 21/9501 250/559.45 |
| 8,144,337 B2* | 3/2012 | Hamamatsu | G01B 11/303 356/600 |
| 8,228,494 B2* | 7/2012 | Shibata | G01N 21/21 356/237.2 |
| 8,310,665 B2* | 11/2012 | Hamamatsu | G01B 11/303 356/237.1 |
| 2006/0192948 A1* | 8/2006 | Judell | G01N 21/21 356/237.2 |
| 2008/0144023 A1* | 6/2008 | Shibata | G01N 21/21 356/237.2 |
| 2008/0151235 A1 | 6/2008 | Oshima et al. | |
| 2009/0290168 A1* | 11/2009 | Hamamatsu | G01B 11/303 356/600 |
| 2010/0225904 A1 | 9/2010 | Oshima et al. | |
| 2010/0265494 A1 | 10/2010 | Oshima et al. | |

FOREIGN PATENT DOCUMENTS

| | | |
|---|---|---|
| JP | 2000-162141 | 6/2000 |
| JP | 2001-083080 | 3/2001 |
| JP | 2008-268140 | 11/2008 |

* cited by examiner (a) DEFECT MAP (b) HAZE MAP

FIG. 7
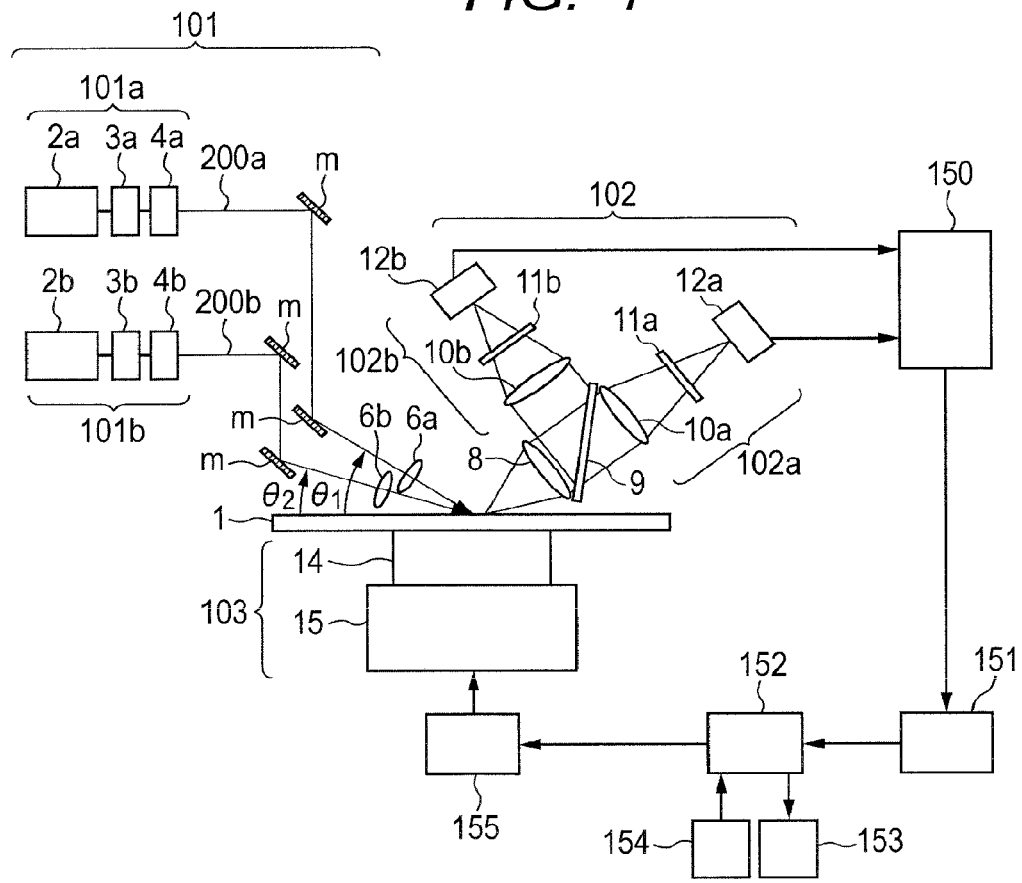
FIG. 8
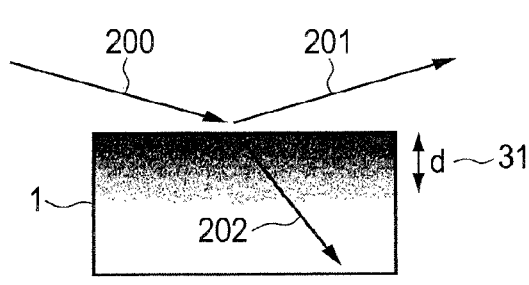
(a)
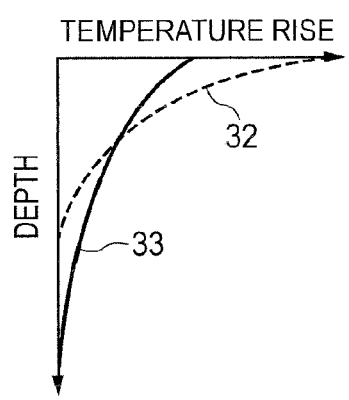
(b)

DEFECT INSPECTING METHOD AND DEFECT INSPECTING APPARATUS

CROSS REFERENCE TO RELATED APPLICATION

This application is a continuation application of U.S. application Ser. No. 14/154,612, filed Jan. 14, 2014, which is a continuation application of U.S. application Ser. No. 13/146,428, filed Jul. 27, 2011 (now U.S. Pat. No. 8,638,429), which is a U.S. National Phase application under 35 U.S.C. §371 of International Application No. PCT/JP2009/006887, filed Dec. 15, 2009, which claims benefit of priority to Japanese Application No. 2009-045857, filed Feb. 27, 2009. The contents of the above applications are incorporated herein by reference.

TECHNICAL FIELD

The present invention relates to a defect inspecting method and a defect inspecting apparatus. More particularly, the invention relates to a surface defect inspecting method and an inspecting apparatus for accurately and fast inspecting tiny defects on a sample surface.

BACKGROUND ART

A production line for semiconductor substrates and membrane substrates inspects defects on surfaces of the semiconductor substrates and membrane substrates in order to ensure and improve product yields. Conventional technologies are disclosed in Japanese Patent Application Laid-Open Publication No. 9-304289 (patent literature 1) and Japanese Patent Application Laid-Open Publication No. 2000-162141 (patent literature 2). In order to detect tiny defects, these technologies condense a laser beam into several micrometers, irradiate the laser beam onto a sample surface, collect and detect scattering light from defects, and detect a defect whose size ranges from nanometers to several micrometers or more.

As semiconductor devices are miniaturized, the required defect detection sensitivity increases accordingly. There have been used sensitivity improvement techniques such as polarization detection of scattering light (patent literature 3). The polarization detection can selectively suppress scattering light (hereafter referred to as roughness scattering light) resulting from sample surface roughness of a laser irradiation portion and improve the detection sensitivity.

In recent years, there is an increasing need to monitor sample surface roughness states other than the defect detection sensitivity. The sample surface roughness is calculated based on the roughness scattering light intensity and is referred to as a haze signal. The haze signal is monitored for process management (non-patent literature 1).

CITATION LIST

Patent Literature

Patent literature 1: Japanese Patent Application Laid-Open Publication No. 9-304289
Patent literature 2: Japanese Patent Application Laid-Open Publication No. 2000-162141
Patent literature 3: U.S. Pat. No. 6,034,776

Non-Patent Literature

Non-patent literature 1: December 2006 Yield Management Solutions, http://www.kla-tencor.com/company/magazine.html

SUMMARY OF INVENTION

Technical Problem

Recently, the LSI wiring is drastically miniaturized. Sizes of defects to be detected approach the detection limit of optical inspection. According to a semiconductor roadmap, mass production of 36 nm node LSI is scheduled to start in 2012. There is a need for capability of detecting a defect as small as a DRAM half pitch. For example, the defect includes a scratch due to a particle or COP (Crystal Originated Particle) attached onto a wafer or due to polishing.

The scattering light occurs when the laser is irradiated to a defect. The relationship of $I \propto d^6$ is known, where I denotes the intensity of the scattering light and d denotes the particle diameter of a defect. That is, reducing the defect size drastically decreases the resulting scattering light. It is necessary to increase the scattering light generated from a fine defect.

Applying a high laser output is a technique of increasing the generated scattering light. However, this technique increases the temperature of an irradiated object and may damage a sample.

As described above, the polarization detection is an effective technique of improving the detection sensitivity while suppressing a temperature rise on the sample surface. However, it is difficult to concurrently ensure the polarization detection and the haze measurement. An inspection apparatus converts the detected scattering light into an electric signal and separates the electric signal into frequency bands. High-frequency components are processed as a defect signal. Low-frequency components are processed as a haze signal. Suppressing the roughness scattering light due to the polarization detection greatly reduces the haze signal and may degrade the haze measurement accuracy and stability.

As seen from the above, problems are: (1) suppressing damage on a wafer; and (2) concurrently improving the defect detection sensitivity using the polarization detection and measuring haze signals.

It is an object of the present invention to provide an inspection method and an apparatus that concurrently improve the defect detection sensitivity using the polarization detection and measure haze signals while suppressing damages on samples.

Solution to Problem

In order to address the above-mentioned problems, the present invention provides a light source, a defect optical detection system, and a haze optical detection system independently of each other. The light source irradiates a laser beam to a sample. The laser beam uses a wavelength band that allows less energy to be absorbed. After the light source irradiates the laser beam, the defect optical detection system detects a defect scattering light occurring from a defect. The haze optical detection system detects a roughness scattering light occurring from a wafer surface roughness. Polarization detection is independently performed on scattering lights detected by the two optical detection systems. Defect determination and haze measurement are performed based on the two different detection signals. When the less energy is absorbed, the energy applied to the wafer is not absorbed in only the very vicinity of the wafer surface, but penetrates into the wafer.

The illumination uses any of wavelengths 405 nm, 488 nm, and 532 nm.

A half mirror, a PBS (Polarized Beam Splitter), or a dichroic mirror performs amplitude separation, polarization separation, or wavelength separation on the scattering light occurring from an irradiated region of the wafer. Then, the defect optical detection system and the haze optical detection system detect the scattering light.

The two different detection systems may use the amplitude separation for the purpose of independent detection. In such a case, switching multiple half mirrors with different transmittances can adjust the amount of scattering light detected by the defect optical detection system and the haze optical detection system.

The two different detection systems may use the wavelength separation for the purpose of independent detection. In such a case, the different detection systems are provided with a light source that oscillates two different wavelengths. The defect optical detection system detects a scattering light resulting from the illumination using one wavelength. The haze optical detection system detects a scattering light resulting from the illumination using the other wavelength.

A single optical detection system may be provided to independently detect a defect signal and a haze signal by using a signal separator to separate and detect the defect signal and the haze signal at different times. The optical detection system does not need amplitude separation, polarization separation, or wavelength separation.

A transmissive polarization axis can be specified for the polarization detection when a user inputs a film type to be inspected and compares the film type with a database. The database is used for the following purpose. Simulation is used to previously calculate polarization states of the defect scattering light and the roughness scattering light while the polarization states vary with film types. The database stores a set of data containing detection conditions for maximizing defect and haze detection sensitivities.

Advantageous Effects of Invention

The present invention can provide a defect inspecting method and apparatus capable of not only increasing irradiation energy while suppressing a temperature rise on the wafer surface, but also improving the sensitivity based on polarization detection and ensuring the haze measurement at the same time. These and other objects, features and advantages of the invention will be apparent from the following more particular description of preferred embodiments of the invention, as illustrated in the accompanying drawings.

BRIEF DESCRIPTION OF DRAWINGS

FIG. 7 is a schematic configuration diagram illustrating a case where two wavelengths are used to illuminate the wafer surface inspection apparatus according to the invention;

FIG. 8 illustrates relation between a penetration depth and a temperature rise;

DESCRIPTION OF EMBODIMENTS

Embodiments of the present invention will be described in further detail with reference to the accompanying drawings.

First Embodiment

Figure 1:
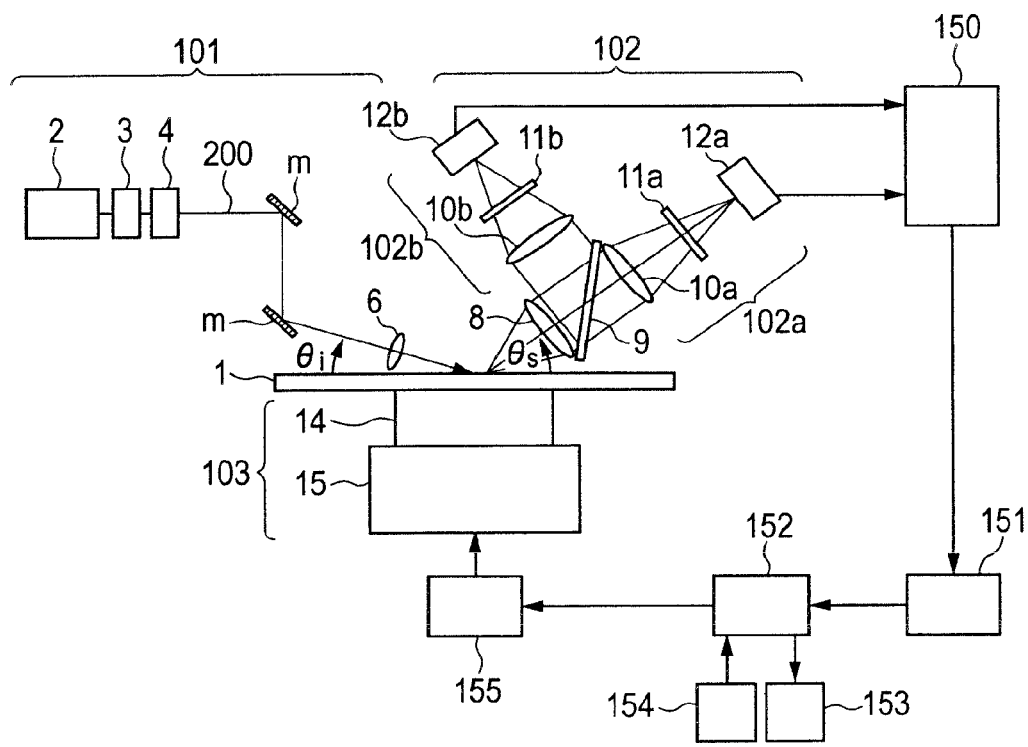
FIG. 1 is a schematic configuration diagram illustrating a wafer surface inspection apparatus according to the invention.

FIG. 1 illustrates an embodiment of the present invention. The configuration in FIG. 1 includes an illuminating optical system 101, an optical detection system 102, a wafer stage 103, a circuit, and a signal processing portion. The illuminating optical system 101 includes a laser light source 2, a beam expander 3, a polarization element 4, a mirror m, and a condensing lens 6. The laser light source 2 irradiates a laser beam 200. The beam expander 3 adjusts the laser beam diameter to a specified size. The polarization element 4 converts the laser beam into a specified polarization state. The laser beam reflects on the reflective mirrors m. Using the reflected laser beam, the condensing lens 6 illuminates an inspection region on the wafer 1.

The laser light source 2 uses an ultraviolet or vacuum ultraviolet laser beam, hardly penetrating the sample inside, in order to detect a defect near (100 nm or less deep from the surface) the surface of the wafer 1. The laser light source 2 uses a visible or infrared laser beam, easily penetrating the sample inside, in order to detect the inside (100 nm or more deep from the surface) of a sample.

The beam expander 3 uses an anamorphic optical system and includes multiple prisms. The beam expander 3 varies a beam diameter in only one direction on a plane orthogonal to the optical axis and uses the condensing lens 6 to provide spot illumination or linear illumination on the wafer 1. Instead of the combination of the condensing lens 6 and the beam expander 3, a cylindrical lens may be used for linear illumination. Just the cylindrical lens enables linear illumination on a wafer without using the anamorphic optical system so as to vary a beam diameter in only one direction on the plane orthogonal to the optical axis. The cylindrical lens is effective for simplifying the optical system because the beam expander 3 may be omitted.

The optical detection system 102 includes a defect optical detection system 102a and a haze optical detection system 102b. A detection lens 8 condenses scattering light that is generated from a laser irradiation portion and is applied to the wafer 1. A beam splitter 9 splits the scattering light into two optical paths. The split scattering light passes through condensing lenses 10a and 10b and filters 11a and 11b. Photomultipliers 12a and 12b detect the scattering light.

The beam splitter 9 provides a half mirror or a PBS, for example. The beam splitter 9 performs amplitude separation or polarization separation on the scattering light that is generated from the laser irradiation portion, applied to the wafer 1, and condensed at the detection lens 8. As a result, the defect optical detection system 102a and the haze optical detection system 102b can independently detect the scattering light.

The filters 11a and 11b use a polarization plate or liquid crystal and are capable of adjusting a polarization axis to be detected. The laser beam 200 having specific polarization characteristics may be irradiated to the wafer. In such a case, the scattering light resulting from a defect or roughness due to the laser irradiation indicates a specific polarization state. The polarization state varies with an illumination condition and a detection condition. The scattering light polarization state can be simulated and calculated. According to respective illumination and detection conditions, it is possible to find polarization axes that easily transmit or eliminate only the defect scattering light or the roughness scattering light. That is, the filter 11a allows the polarization axis to be adjusted to easily transmit only the defect scattering light. The filter 11b allows the polarization axis to be adjusted to easily transmit only the roughness scattering light. As a result, the defect optical detection system 102a can detect the scattering light resulting from a defect with high sensitivity. The haze optical detection system 102b can detect only the roughness scattering light with high sensitivity.

Figure 2:
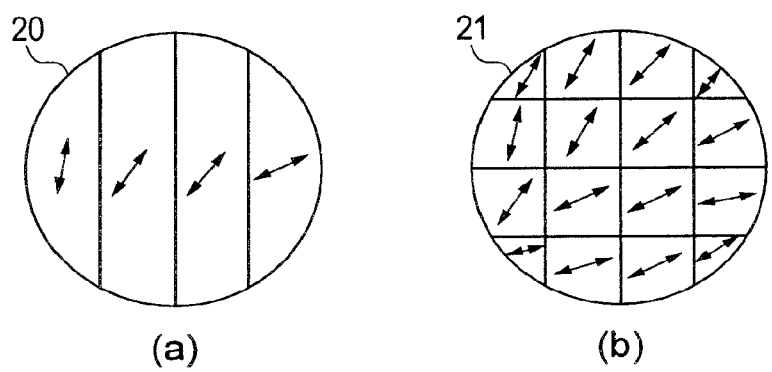
FIG. 2 is a schematic configuration diagram illustrating a filter.

As shown in FIG. 2, the filters 11a and 11b are divided into segments. The segments each may have different polarization axes. FIG. 2A exemplifies a filter 20 where the polarization axis varies one-dimensionally. FIG. 2B exemplifies a filter 21 where the polarization axis varies two-dimensionally. The examples do not limit the number of divided segments, the division method, or polarization axis directions.

The beam splitter 9 uses different transmittances. Changing the transmittances can adjust the sensitivity of the defect optical detection system and the haze optical detection system. For example, the defect optical detection system 102a is provided with the transmittance of 50%. The haze optical detection system 102b is provided with the reflectance of 50%. When the defect detection sensitivity is below the required level, the transmittance for the defect optical detection system 102a is changed to 90%. The reflectance for the haze optical detection system 102b is changed to 10%. The change increases the scattering light the defect optical detection system can detect. Accordingly, the defect detection sensitivity can be improved.

The photomultipliers 12a and 12b are used to receive and photoelectrically convert the scattering light. The photomultipliers 12a and 12b may be replaced by a TV camera, a CCD camera, a photodiode, a linear sensor, a sensitive image sensor using an image intensifier combined with these devices, or a multi-anode photomultiplier. For example, a two-dimensional sensor can inspect a wide region at one.

The photomultipliers 12a and 12b generate an electric signal corresponding to the amount of received light. The electric signal is supplied to an analog circuit 150. The following describes a process performed on the analog circuit 150.

Figure 3:
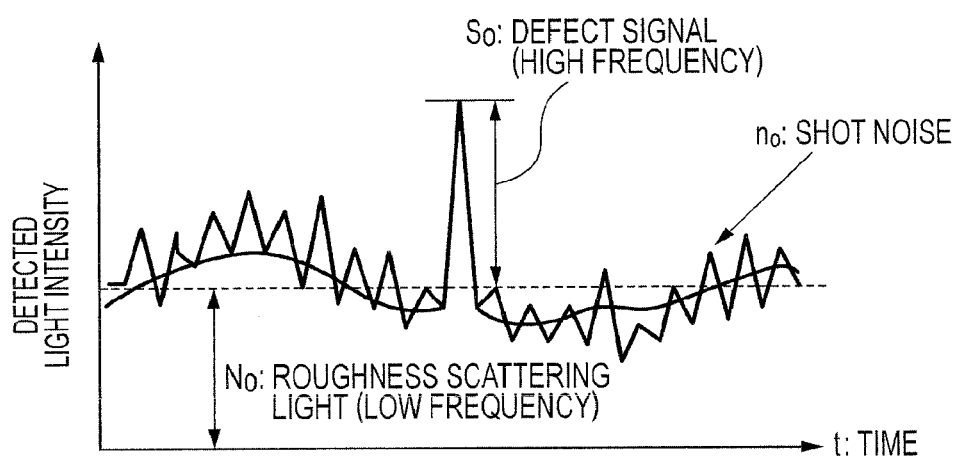
FIG. 3 is an explanatory diagram illustrating a detection signal.

Due to the laser irradiation, a signal as shown in FIG. 3 is detected from the irradiated portion. Roughness scattering light N0 results from a surface roughness. During the laser irradiation, the roughness scattering light N0 is always generated and is detected as a low-frequency surge (less than several kilohertz). Shot noise n0 occurs as random fluctuation when the roughness scattering light N0 enters the photomultiplier and is photoelectrically converted. The shot noise n0 is also detected at the same time. On the other hand, defect scattering light S0 occurs in pulses from a defect only during a time when the beam, several tens of micrometers wide, passes through a position corresponding to the defect. The defect scattering light S0 indicates a higher frequency than the roughness scattering light (more than several kilohertz). When the detection signal as shown in FIG. 3 is applied to the analog circuit, the detection signal passes through a high-pass filter to be able to extract a defect signal and passes through a low-pass filter to be able to extract a haze signal.

Figure 4:
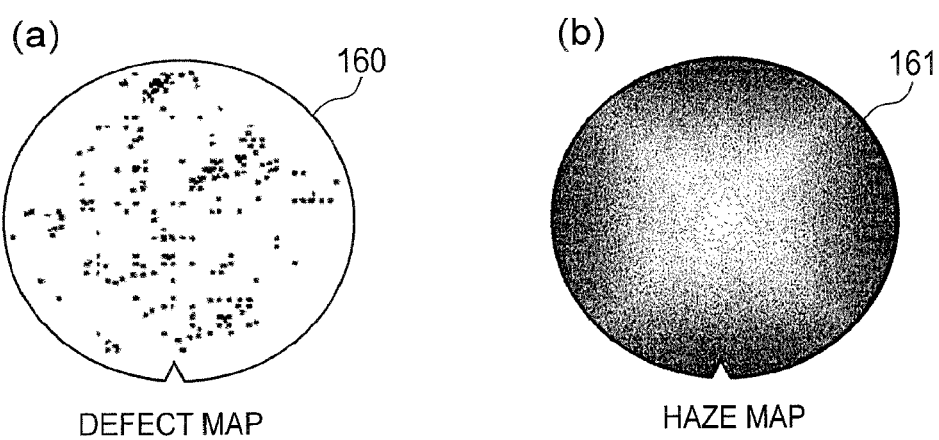
FIG. 4 exemplifies a defect map and a haze map.

Accordingly, the high-pass filter is applied to an electric signal that occurs based on the defect scattering light detected by the photomultiplier 12a. The low-pass filter is applied to an electric signal that occurs based on the roughness scattering light detected by the photomultiplier 12b. The analog circuit 150 further amplifies the electric signal and converts it from analog to digital. Based on the detection signal, a signal processing portion 151 performs defect determination based on a threshold process and performs a haze process based on level determination. A CPU 152 allows a map output portion 153 to display a defect map 160 and a haze map 161 as shown in FIG. 4. The defect map 160 is displayed based on the defect signal received during the inspection and coordinates. The haze map 161 is displayed based on the haze signal received during the inspection and coordinates. An input portion 154 includes a user interface, enabling a user to configure a recipe.

The wafer stage 103 includes a Z stage (not shown), a rotation stage 14, and a translation stage 15. The Z stage controls a chuck and height for holding the wafer 1. The rotation stage 14 rotates the wafer. The translation stage 15 moves the wafer in a radial direction. The wafer stage 103 performs rotational scan and translational scan so that the laser beam spirally irradiates the entire surface of the wafer. A stage control portion 155 controls a rotation speed and a translation speed so as to be able to irradiate an intended region.

The example in FIG. 1 uses one illuminating optical system 101 and one optical detection system 102 for the description above. Multiple illuminating optical systems and optical detection systems may be used in multiple elevation angles (not shown). For example, an oblique illuminating optical system illuminates a wafer at a low elevation angle θ1. A vertical illuminating optical system illuminates a wafer approximately vertically to it. A low-angle optical detection system detects a defect at a low elevation angle θs against a wafer. A high-angle optical detection system detects a defect at an elevation angle higher than that of the low-angle optical detection system against a wafer.

The oblique illuminating optical system generates a larger scattering cross-section for a foreign particle than the vertical illuminating optical system when illuminating the particle attached onto the wafer. Accordingly, the oblique illuminating optical system increases the amount of scattering light generated from a defect and effectively improves the sensitivity. The scattering light from a defect of a size of several tens of nanometers strongly scatters to the side of a low elevation angle. The scattering light from a defect of a size of 100 nanometers or more strongly scatters to the side of a high elevation angle. The low elevation angle optical detection system is configured to detect tiny defects. The high elevation angle optical detection system is configured to detect larger defects. It is possible to increase the range of detectable defect sizes.

The vertical illuminating optical system increases a scattering cross-section when illuminating a recessed defect such as a COP or a scratch on the wafer. The vertical illuminating optical system can improve the sensitivity of detecting recessed defects. The scattering light from a recessed defect strongly scatters to the side of a high elevation angle. The high elevation angle optical detection system can further improve the detection sensitivity.

As described above, the intensity distribution of the scattering light occurring from a defect or elevation angle characteristics vary with defect types such as particle, COP, and scratch and defect sizes. The accuracy of classifying defects or calculating defect sizes can be improved by combining and comparing signals in the illumination directions and the detection directions.

Figure 5:
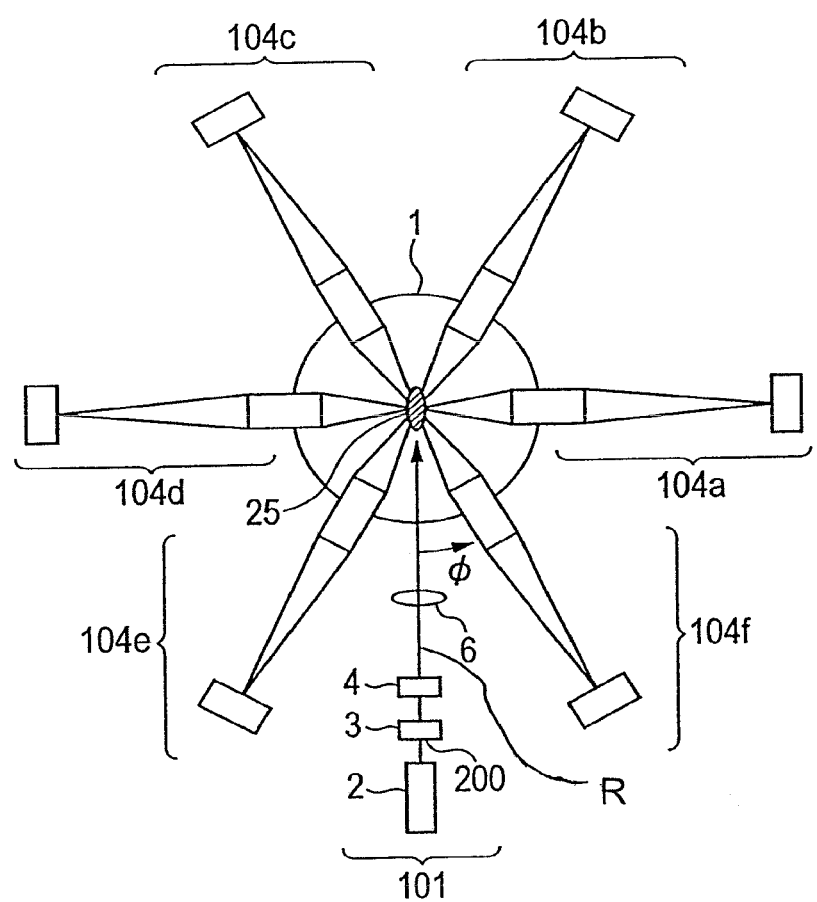
FIG. 5 is a schematic configuration diagram illustrating multiple optical detection systems in different azimuthal directions.

FIG. 5 is an example plan view of the embodiment shown in FIG. 1. As shown in FIG. 5, multiple optical detection systems may be provided in different azimuthal directions ϕ. The example includes the wafer 1, the illuminating optical system 101, optical detection systems 104a through 104f, and an illumination spot 25. The optical detection systems 104a through 104f each include the defect optical detection system 102a and the haze optical detection system 102b. The analog circuit 150 amplifies a detection signal, removes a noise from it, and converts it from analog to digital. The optical detection systems 104a through 104f add scattering light signals to each other that occurred when approximately the same region was illuminated. The signal processing portion 151 determines a defect and a haze based on the added signal. The CPU 152 allows the map output portion 153 to display the defect map 160 and the haze map 161.

There has been described the embodiment that uses the optical detection systems in multiple azimuthal directions. Since the optical detection systems are provided at multiple azimuth angles, there is the advantage of improving the defect detection sensitivity by selecting the optical detection system to be used or weighting a detection signal for each detection. The roughness scattering light varies with azimuth angles depending on roughness states on the wafer surface. For example, an Si wafer having the very smooth surface tends to generate the strong roughness scattering light in an incident direction of the laser beam 200, that is, in an azimuthal direction along which the optical detection systems 104e and 104f are provided. An Al-deposit wafer having the coarse surface tends to generate the strong roughness scattering light in a direction of advancing the laser beam 200, that is, in an azimuthal direction along which the optical detection systems 104b and 104c are provided. To improve the defect detection sensitivity, a possible technique uses only the detection signal detected in the defect optical detection system provided along the azimuth angle at which the weak roughness scattering light occurs. Another technique uses a weight equivalent to the roughness scattering light intensity and multiplies the weight as a gain by the detection signal for processing.

FIG. 5 shows the example of placing six optical detection systems in different azimuthal directions. The number of optical detection systems is not limited to six. The azimuthal directions for placing the optical detection systems are not limited. Multiple optical detection systems need not be placed at approximately the same elevation angle θs. A detector need not be placed approximately at the same azimuth angle.

FIG. 5 shows the laser irradiation from the direction parallel to the longer direction of the illumination. The longer direction of the illumination need not approximately equal the laser irradiation direction. The illumination may be provided from a different direction. The illumination from different directions provides the advantage of improving the performance of classifying defects such as scratches that are shaped directionally. The scattering light is independent of the azimuth angle when the scattering light occurs from a COP or similar defects approximately symmetric about the azimuthal direction. The scattering light occurs almost uniformly in all azimuthal directions. On the other hand, the scattering light is dependent on the azimuth angle when the scattering light occurs from a scratch or similar defects not symmetric about the azimuthal direction. The azimuthal characteristics of the scattering light from scratches also depend on the azimuth angle for the incident illumination. It is possible to improve the accuracy of classifying defects or calculating sizes by actively varying illumination directions and comparing detection-related signals available in azimuthal directions.

A signal processing method adds or averages detection signals from detectors provided in the directions of multiple azimuth angles and elevation angles. Adding signals increases the amount of detected light and effectively improves the detection sensitivity. Averaging signals increases a range of detectable sizes within the dynamic range of a sensor and effectively enhances the dynamic range.

Figure 6:
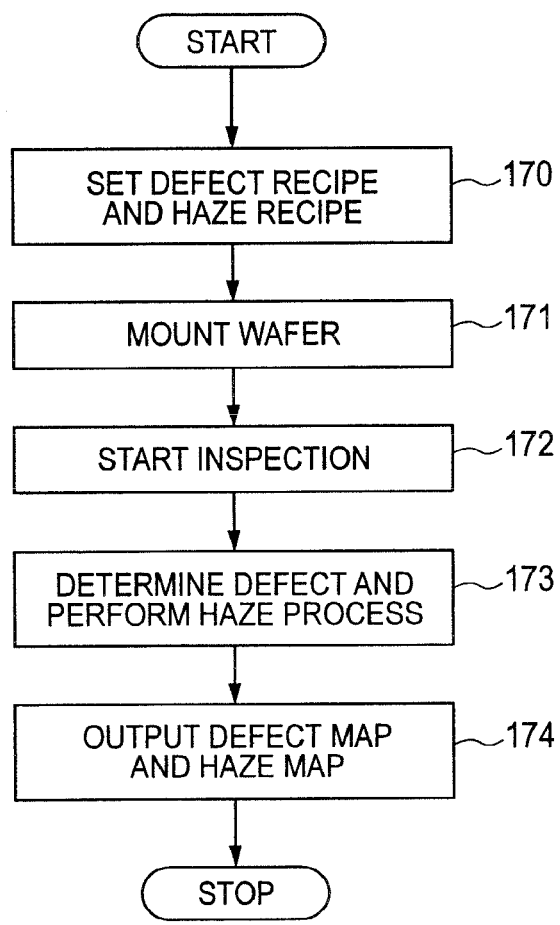
FIG. 6 shows an inspection flowchart for the inspection apparatus.

The following describes a flow of a defect detection process with reference to FIG. 6. The recipe setting configures inspection conditions such as an illumination direction, illumination energy, and sensor sensitivity. The recipe setting includes not only a defect detection recipe but also a haze measurement recipe (step 170). A wafer is mounted on the stage (step 171). The inspection starts (step 172). A defect is determined based on a detection signal (step 173). A defect map and a haze map are displayed (step 174).

Second Embodiment

The following describes the second embodiment of the invention with reference to FIG. 7. Basically, an example in FIG. 7 includes the illuminating optical system 101, the optical detection system 102, the wafer stage 103, the circuit, and the signal processing portion.

The illuminating optical system 101 includes illuminating optical systems 101a and 101b. The illuminating optical system 101a includes a light source 2a that oscillates a laser beam with the wavelength of λ1. The illuminating optical system 101b includes a light source 2b that oscillates a laser beam with the wavelength of λ2 different from λ1. The respective light sources oscillate laser beams 200a and 200b. Beam expanders 3a and 3b adjust diameters of the laser beams 200a and 200b to specified sizes. Polarization elements 4a and 4b convert the laser beams into specified polarization states. The laser beams are reflected on the mirror m and pass through condensing lenses 6a and 6b so as to be irradiated to approximately the same region on the wafer 1.

The beam splitter 9 according to the second embodiment may use a wavelength separation element such as a dichroic mirror. The defect optical detection system 102a detects the defect scattering light that occurs from a defect illuminated by the laser beam 200a with the wavelength of λ1. The haze optical detection system 102b detects the defect scattering light that occurs from a surface roughness illuminated by the laser beam 200b with the wavelength of λ2.

The following describes the advantage of using two different wavelengths to independently detect the defect scattering light and the roughness scattering light.

FIG. 8(a) schematically shows that the laser beam 200 is irradiated to the wafer 1 and the wafer 1 absorbs an irradiation energy. Part of the irradiation energy (201) is reflected when the wafer 1 is illuminated. The remaining energy as transmitted light 202 penetrates into the wafer 1. The penetrated energy 202 continues to penetrate into the wafer 1 and is gradually absorbed as heat by the wafer 1. The energy of the transmitted light 202 attenuates down to $(1/e)^2$ at distance d 31 from the surface after the penetration. The distance is hereafter referred to as a penetration depth. The energy is absorbed only in the surface layer when the penetration depth is small. The energy penetrates into the wafer 1 when the penetration depth is large.

FIG. 8(b) shows relation between the depth direction and the temperature of two materials with different penetration depths. A curve 32 illustrates an example of the material with a small penetration depth. The energy is absorbed near the surface of the wafer 1. The temperature rises greatly on the surface of the wafer 1. A curve 33 illustrates an example of the material with a large penetration depth. The energy penetrates into the wafer 1. The temperature rises moderately on the surface of the wafer 1. The material represented by the curve 32 more increases the temperature on the surface of the wafer 1 than the material represented by the curve 33 when approximately the same energy is applied to the materials represented by the curves 32 and 33. The penetration depth varies with materials and illumination wavelengths.

Increasing the irradiation energy is effective for improving the defect detection sensitivity. The description about the penetration depth above makes it clear that increasing the irradiation energy requires laser irradiation using a light source whose wavelength causes a large penetration depth in wafers.

The following describes an example of illuminating an Si wafer using wavelengths of 355 nm and 532 nm. Illuminating the Si wafer using the wavelength of 355 nm causes a penetration depth of approximately 10 nm. Illuminating the Si wafer using the wavelength of 532 nm causes a penetration depth of approximately 2 μm. From the viewpoint of the penetration depth, it is clear that the illumination using the wavelength of 532 nm suppresses the temperature from rising and increases the irradiation energy.

The following describes relation between the haze measurement and the penetration depth.

For the haze measurement, it is desirable to detect only the roughness scattering light occurring nearly from the surface roughness. The scattering light occurring from a COP contained in the sample may be detected as well when the illumination uses the wavelength causing a large penetration depth. The haze measurement accuracy or stability may degrade.

It is desirable to use the wavelength causing a small penetration depth for illumination and detect only the roughness scattering light occurring nearly from the surface roughness in order to ensure the haze measurement accuracy or stability.

As will be understood from the above, the illumination needs to use a wavelength causing a large penetration depth in order to improve the particle detection sensitivity. The illumination needs to use a wavelength causing a small penetration depth in order to improve the haze measurement accuracy and stability.

For example, wavelengths of 405 nm, 488 nm, and 532 nm cause large penetration depths in Si wafers. Wavelengths of 355 nm and 266 nm cause small penetration depths in Si wafers.

According to the example in FIG. 7, there has been described that the incident elevation angle θ1 for the illuminating optical system 101a differs from the incident elevation angle θ2 on the wafer for the illuminating optical system 101a. There are no limitations on the two incident elevation angles. There are no limitations on the incident azimuth angles of the two laser beams.

While there has been described the example using one optical detection system 102, multiple optical detection systems may be used. There are no limitations on elevation angles or azimuth angles for detection by the optical detection systems.

Third Embodiment

Figure 9:
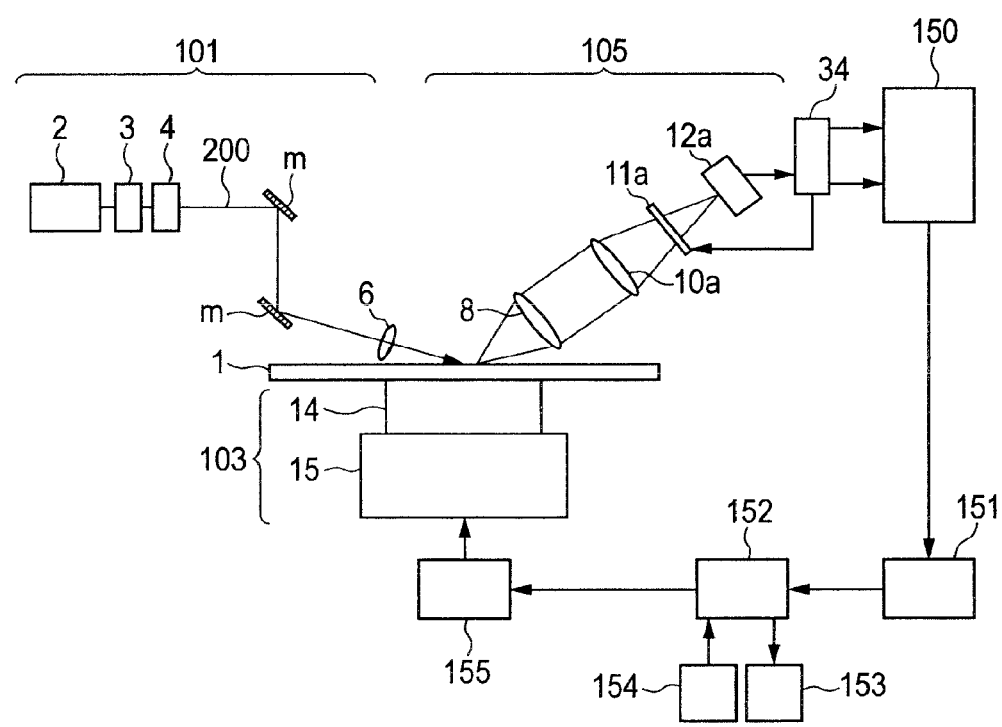
FIG. 9 is a schematic configuration diagram illustrating time sharing detection on the wafer surface inspection apparatus according to the invention.

The following describes the third embodiment of the invention with reference to FIG. 9. Basically, an example in FIG. 9 includes the illuminating optical system 101, an optical detection system 105, the wafer stage 103, the circuit, and the signal processing portion.

The optical detection system 105 includes the detection lens 8, a condensing lens 10a, and a filter 11a. A photomultiplier 12a detects the scattering light.

The filter 11a uses a polarization plate or liquid crystal and is provided with a polarization axis capable of easily transmitting only the defect scattering light. As will be described later, the filter 11a synchronizes with a signal separator 34 and is configured to be able to enable or disable the polarization axis rotation or filtering.

The signal separator 34 turns on or off a gate circuit to switch a detection signal from the photomultiplier 12a to two paths for the defect signal and the haze signal at specified timings. In this manner, the detection signal is separated and detected.

Figure 10:
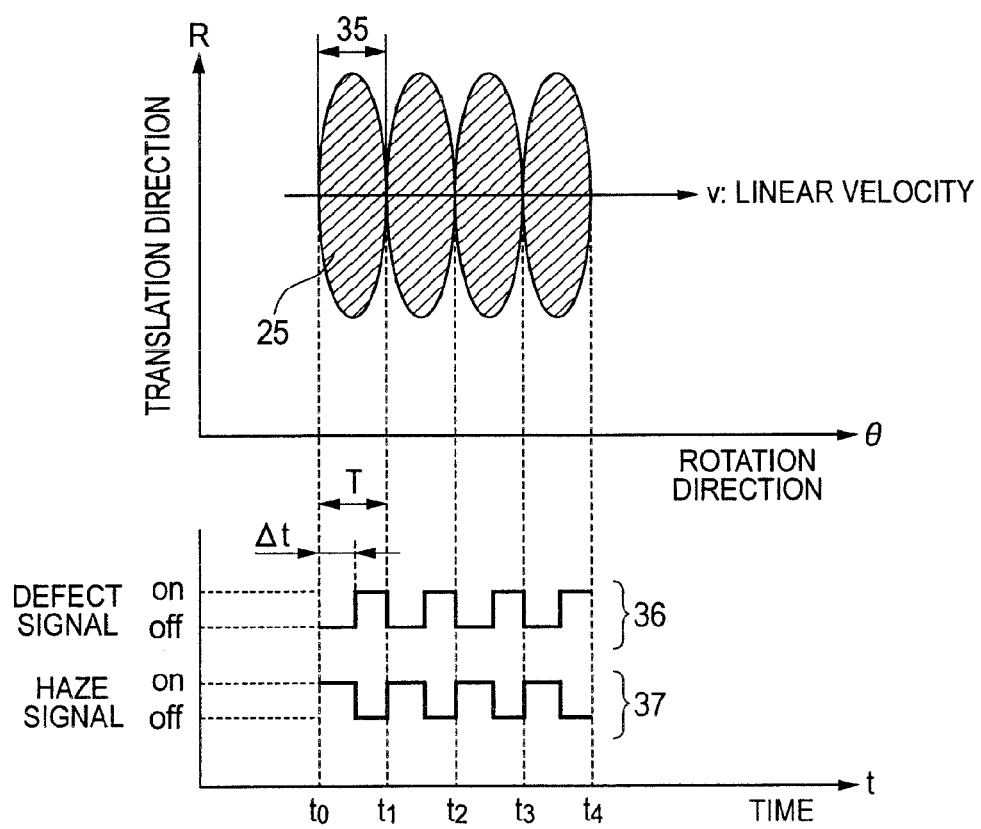
FIG. 10 is an explanatory diagram illustrating timings to turn on or off a gate circuit in a signal separator.

The following describes switch timings for the signal separator with reference to FIG. 10. FIG. 10 shows relation between movement of the illumination spot 25 irradiated on the wafer during a scan using the rotation stage and gate circuit timings to turn on or off the defect signal and the haze signal in the signal processing portion. The R axis represents the movement direction of the translation stage 15. The θ axis represents the rotation direction of the rotation stage 14. The illumination spot 25 occupies a region whose area is several tens of square micrometers. The region for the illumination spot 25 is too small for the area of the wafer whose diameter is 300 mm. There is no problem with the explanatory diagram in FIG. 10 where the R axis and the θ axis cross each other at right angles. The rotation stage 14 rotates at linear velocity v and requires time T: (t1−t0) to pass through a length 35 of the illumination spot in a shorter direction. Based on T0 as a reference, the gate circuit is switched to process the detection signal as the defect signal only during a period of Δt (<T). The gate circuit is switched to process the detection signal as the haze signal only during a period of (T−Δt). The detection signal is also processed as the defect signal only during the period of Δt and as the haze signal only during the period of (T−Δt) from t1, t2, and t3, thereafter. The size of Δt is equivalent to a time period ranging from several hundreds of nanoseconds to several microseconds. Since the gate circuit is switched at the above-mentioned timings, a single detection system can provide effects of the defect optical detection system and the haze optical detection system without leaving a region that is not detected. The optical detection system is omissible, thus reducing costs and decreasing the installation space.

The filter 11a includes the polarization axis that easily transmits only the defect scattering light and therefore greatly eliminates the scattering light from the surface roughness when the haze signal is received. A servo motor rotates the polarization axis of the filter 11a in synchronization with the gate circuit switchover timings while the signal separator 34 processes the detection signal as the haze signal. The polarization state is conditioned to easily transmit only the scattering light from the surface roughness. The filtering and the polarization detection may be omitted when the haze signal is received.

Extending the time Δt increases the defect detection signal and decreases the haze detection signal. Shortening the time Δt decreases the defect detection signal and increases the haze detection signal. Adjusting the time Δt can adjust the intensity of the defect detection signal and the haze detection signal.

The PMT 12a generates an electric signal corresponding to the amount of received light. The signal separator 34 separates the electric signal into the defect detection signal and the haze detection signal. The analog circuit 150 amplifies the detection signals, removes a noise from them, and converts them from analog to digital as needed. The signal processing portion 151 determines a defect and a haze. The CPU 152 allows the map output portion 153 to display the defect map 160 and the haze map 161.

While there has been described the example using one optical detection system 105, multiple optical detection systems may be used. There are no limitations on elevation angles or azimuth angles for detection by the optical detection systems.

Fourth Embodiment

Figure 11:
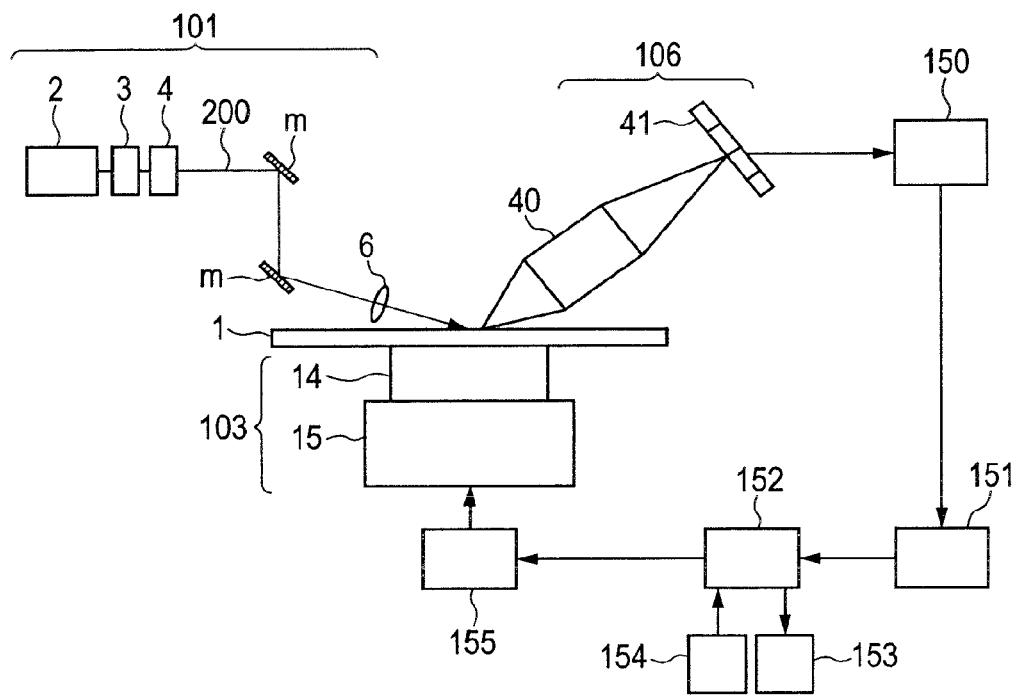
FIG. 11 is a schematic configuration diagram illustrating multiple pixel sensors used for the wafer surface inspection apparatus according to the invention.

The following describes the fourth embodiment of the invention with reference to FIG. 11. Basically, an example in FIG. 11 includes the illuminating optical system 101, an optical detection system 106, the wafer stage 103, the circuit, and the signal processing portion. The illuminating optical system 101 includes the laser light source 2, the beam expander 3, the polarization element 4, the mirror m, and the condensing lens 6. The laser light source 2 irradiates the laser beam 200. The beam expander 3 adjusts the laser beam diameter to a specified size. The polarization element 4 converts the laser beam into a specified polarization state. The condensing lens 6 illuminates an inspection region on the wafer 1.

The beam expander 3 uses an anamorphic optical system and includes multiple prisms. The beam expander 3 varies a beam diameter in only one direction on a plane orthogonal to the optical axis and uses the condensing lens 6 to provide spot illumination or linear illumination on the wafer 1. Instead of the combination of the condensing lens 6 and the beam expander 3, a cylindrical lens may be used for linear illumination. Just the cylindrical lens enables linear illumination on a wafer without using the anamorphic optical system so as to vary a beam diameter in only one direction on the plane orthogonal to the optical axis. The cylindrical lens is effective for simplifying the optical system because the beam expander 3 may be omitted.

Figure 12:
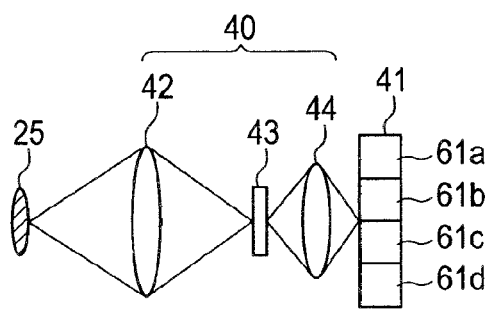
FIG. 12 is an explanatory diagram illustrating in detail an imaging system.

The optical detection system 106 includes an imaging optical system 40 and a photodiode array 41. FIG. 12 shows in detail the optical detection system 106. The optical detection system 106 includes a condensing lens 42, an image intensifier 43, and imaging lenses 44 and 41. The condensing lens 42 condenses the light scattered from the illumination spot 25. The image intensifier 43 amplifies the scattering light. The scattering light passes through the imaging lens 44 and is imaged onto the photodiode array 41. The photodiode includes pixels 61a through 61d.

The photodiode array 41 generates an electric signal corresponding to the amount of received light. The analog circuit 150 amplifies the electric signal, removes a noise from it, and converts it from analog to digital. The signal processing portion 151 determines a defect and a haze. The CPU 152 allows the map output portion 153 to display the defect map 160 and the haze map 161. The input portion 154 allows a user to configure a recipe.

The wafer stage 103 includes a Z stage (not shown), a rotation stage 14, and a translation stage 15. The Z stage controls a chuck and height for holding the wafer 1. The rotation stage 14 rotates the wafer. The translation stage 15 moves the wafer in a radial direction. The wafer stage 103 performs rotational scan and translational scan so that the laser beam spirally irradiates the entire surface of the wafer. The stage control portion 155 controls a rotation speed and a translation speed so as to be able to irradiate an intended region.

The stage is translated at an approximate constant speed in the radial direction (R direction). A feeding pitch signifies a distance traveled in the radial direction after the stage rotates approximately one revolution. The stage is rotated and translated to enable the scan so that the illumination spot spirally moves on the entire wafer surface. The length of the illumination spot 25 in the radial direction approximately equals the feeding pitch. In many cases, one defect is illuminated only once.

The present invention uses linear illumination. The same defect is illuminated more than once by configuring the length of the illumination spot 25 in the radial direction to be longer than the feeding pitch. The inspection method will be described below.

Figure 13:
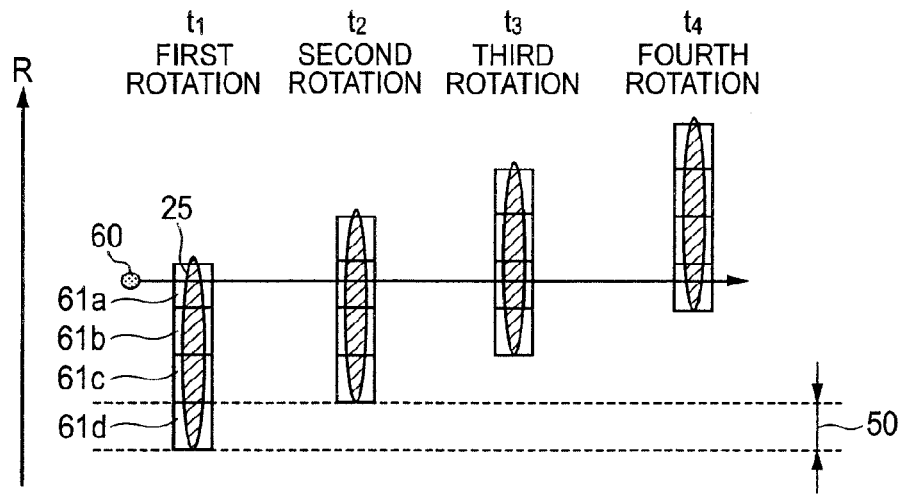
FIG. 13 is an explanatory diagram illustrating an inspection method of illuminating the same defect more than once.

According to the explanatory diagram in FIG. 13, the length of the illumination spot 25 in the radial direction is four times longer than a feeding pitch 50. A defect 60 is illuminated four times. Multiple illuminations will be described with reference to FIG. 13. At time t1, the first illumination is performed on the defect 60 at the illumination spot 25. The pixel 61a detects the scattering light occurring from the defect. At time t2, the wafer rotates approximately one revolution. The illumination spot 25 travels the distance approximately corresponding to the feeding pitch 50 in the radial direction. The defect 60 is re-illuminated. The pixel 61b detects the scattering light from the defect. At times t3 and t4, the wafer rotates approximately one revolution to illuminate the defect 60. The pixels 61c and 61d detect the scattering light from the defect. As a result, the defect 60 can be illuminated four times according to the method shown in FIG. 13. The analog circuit or the signal processing portion adds or averages the detected scattering lights. The illumination is not limited to four times and may be performed any number of times. Increasing the number of additions can amplify the scattering light signal from a defect and improve the detection sensitivity.

The photodiode 41 is not limited to include four pixels.

Figure 14:
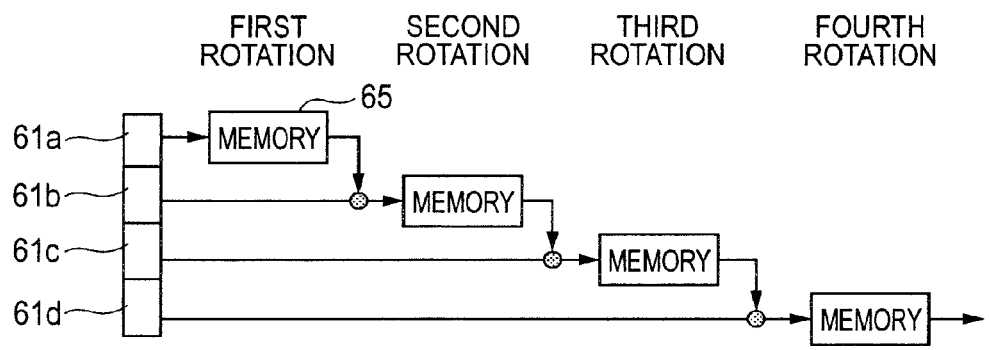
FIG. 14 is an explanatory diagram illustrating a signal processing portion that illuminates the same defect more than once.

The following describes an addition process method in the signal processing portion with reference to FIG. 14. The present invention assumes that each of the pixels detects approximately the same region and shifts one by one each time the wafer rotates one revolution. Accordingly, the memory for storing the detection signal is shifted each time the wafer rotates one revolution. The memory 65 stores a signal for the pixel 61a at the first rotation. Thereafter, the memory 65 stores a signal for the pixel 61b at the second rotation. The memory 65 stores a signal for the pixel 61c at the third rotation. The memory 65 stores a signal for the pixel 61d at the fourth rotation. This makes it possible to add signals from approximately the same region.

While there has been described the example using one optical detection system 106, multiple optical detection systems may be used. There are no limitations on elevation angles or azimuth angles for detection by the optical detection systems.

The image intensifier 43 is used in order to amplify and detect a weak scattering light. Instead of the image intensifier, for example, it is also preferable to use an EM-CCD, a multi-anode photomultiplier, or an equivalent sensor that indicates a high amplification factor itself. These devices are effective for miniaturization of the apparatus because the optical detection system can be provided in a small space.

The photodiode array 41 is used to receive and photo-electrically convert the scattering light. The photodiode array 41 may be replaced by a TV camera, a CCD camera, a photodiode, a linear sensor, a sensitive image sensor using an image intensifier combined with these devices, or a multi-anode photomultiplier.

Fifth Embodiment

A modification of the fourth embodiment will be described with reference to FIG. 15.

The embodiment varies polarization state of the scattering light that can be detected for each pixel of the photodiode 41. In addition, the embodiment varies the method of switching the storage memory to be added in the signal processing portion. FIG. 15 shows an example of the photodiode array 41 including four pixels 61a through 61d. Filters 74a and 74b are polarization plates having polarization axes that easily transmit only the defect scattering light. Filters 75a and 75b are polarization plates having polarization axes that easily transmit only the roughness scattering light.

The detector is provided at an azimuth angle for detection approximately perpendicular to the illumination direction and uses the following examples of polarization axes that easily transmit only the defect scattering light and the roughness scattering light. A polarization axis perpendicular to the wafer provides a polarization detection angle that easily transmits the defect scattering light. An angle of approximately 45 degrees from the direction perpendicular to the wafer provides a polarization detection angle that easily transmits the roughness scattering light.

Attaching a filter 74a to a photosensitive surface of the pixel 61a configures a defect detection pixel 70a. The filter 74a includes the polarization axis that easily transmits only the defect scattering light. Accordingly, the defect detection pixel 70a detects only the defect scattering light. Similarly, a defect detection pixel 70b includes the pixel 61b and a filter 74b and highly sensitively detects only the defect scattering light.

Attaching a filter 75a to a photosensitive surface of the pixel 61b configures a haze detection pixel 71a. The filter 75a includes the polarization axis that easily transmits only the roughness scattering light. Accordingly, the haze detection pixel 70a detects only the roughness scattering light. Similarly, a haze detection pixel 71b includes the pixel 61b and a filter 75b and highly sensitively detects only the roughness scattering light.

Figure 15:
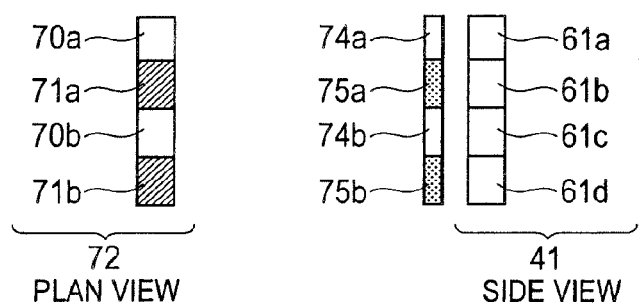
FIG. 15 is an explanatory diagram illustrating defect detection pixels and haze detection pixels.

As shown in FIG. 15, a photodiode array 72 alternately includes the defect detection pixels and haze detection pixels.

Figure 16:
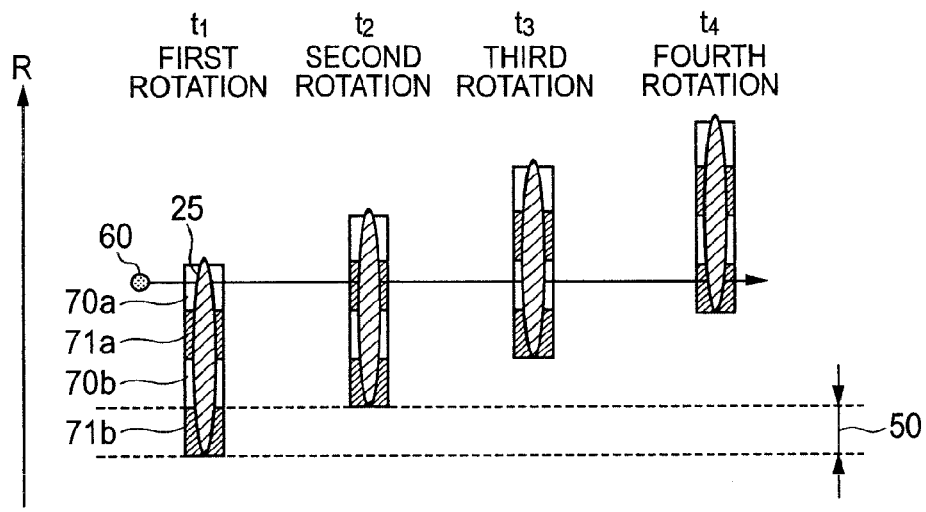
FIG. 16 is an explanatory diagram illustrating an inspection method using a photodiode shown in FIG. 14.

The following describes a scan method using the photodiode 72 with reference to FIG. 16. As shown in FIG. 16, the length of the illumination spot 14 in the radial direction is four times longer than the feeding pitch 50. The defect 60 is illuminated four times. At time t1, the first illumination is performed on the defect 60 at the illumination spot 25. The scattering light occurs from a defect or a surface roughness and is condensed at the defect detection pixel 70a. The defect detection pixel 70a is provided with a filter that easily transmits only the defect scattering light. Accordingly, the defect detection pixel 70a eliminates the roughness scattering light and detects a defect signal.

At time t2, the wafer approximately rotates one revolution. The second illumination is performed on the defect 60 at the illumination spot 25. The scattering light occurs from a defect or a surface roughness and is condensed at the haze detection pixel 71a. The haze detection pixel 71a is provided with a filter that easily transmits only the roughness scattering light. Accordingly, the haze detection pixel 71a eliminates the defect scattering light and detects a haze signal.

At time t3, the wafer approximately rotates one revolution. The third illumination is performed on the defect 60 at the illumination spot 25. The scattering light occurs from a defect or a surface roughness and is condensed at the defect detection pixel 70b. The defect detection pixel 70b is provided with a filter that easily transmits only the defect scattering light. Accordingly, the defect detection pixel 70b eliminates the roughness scattering light and detects a defect signal.

At time t4, the wafer approximately rotates one revolution. The fourth illumination is performed on the defect 60 at the illumination spot 25. The scattering light occurs from a defect or a surface roughness and is condensed at the haze detection pixel 71b. The haze detection pixel 71a is provided with a filter that easily transmits only the roughness scattering light. Accordingly, the haze detection pixel 71a eliminates the defect scattering light and detects a haze signal.

The photodiode 72 may be used when the same foreign particle is illuminated several times and multiple detected signals are added. In such a case, the defect scattering light and the roughness scattering light are alternately detected each time the wafer rotates one revolution. That is, it is also necessary to change the method of switching the memory that stores a detection signal corresponding to one revolution.

Figure 17:
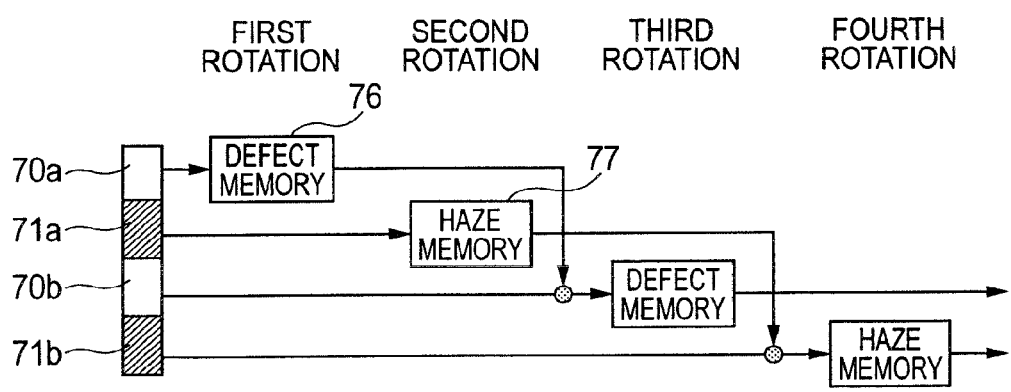
FIG. 17 is an explanatory diagram illustrating a signal processing portion that uses the photodiode shown in FIG. 14.

The following describes an addition process method in the signal processing portion 151 with reference to FIG. 17. The signal processing portion 151 includes defect signal storage memory 76 and haze signal storage memory 77.

The defect signal storage memory 76 stores a signal detected by the defect detection pixel 70a at the first revolution. The haze signal storage memory 77 stores a signal detected by the haze detection pixel 71a at the second revolution. The defect signal storage memory 76 stores a signal detected by the defect detection pixel 70b at the third revolution. The haze signal storage memory 77 stores a signal detected by the haze detection pixel 71b at the fourth revolution.

As described above, the photodiode array 72 uses two types of pixels, the defect detection pixels 70a and 70b and the haze detection pixels 71a and 71b. The defect signal storage memory 76 and the haze signal storage memory 77 are provided and store the detection signals. As a result, it is possible to not only improve the defect detection sensitivity based on the polarization detection, but also ensure the haze measurement at the same time.

The embodiment provides the example of the sensor having four pixels of which two defect detection pixels and two haze detection pixels are laid out alternately. There are no limitations on the number of photodiodes, a ratio of the defect detection pixels and the haze detection pixels, or the order of placing these pixels.

For example, there may be an example of providing three defect detection pixels and one haze detection pixel. The example can increase the number of defect signal detections up to three. The example provides an effect of improving the defect detection sensitivity.

According to the above-mentioned example, the filters 74a and 74b are provided with the polarization axis that easily transmits the defect scattering light. One of the filters may not be configured to most easily transmit the defect scattering light. However, the dynamic range for the sensor is limited. A sensor output may be saturated if the large scattering light occurs from a large foreign particle when the sensitivity is increased to detect a tiny defect. The defect size is calculated based on the amount of detected light. The accuracy of defect size calculation degrades if a sensor output is saturated. To solve this problem, the polarization axis of the filter provided for the defect detection pixel is shifted from the polarization axis that most easily transmits the defect scattering light. The scattering light occurring from a large foreign particle can be detected without saturating the sensor output. There is provided an effect of increasing the dynamic range.

Figure 18:
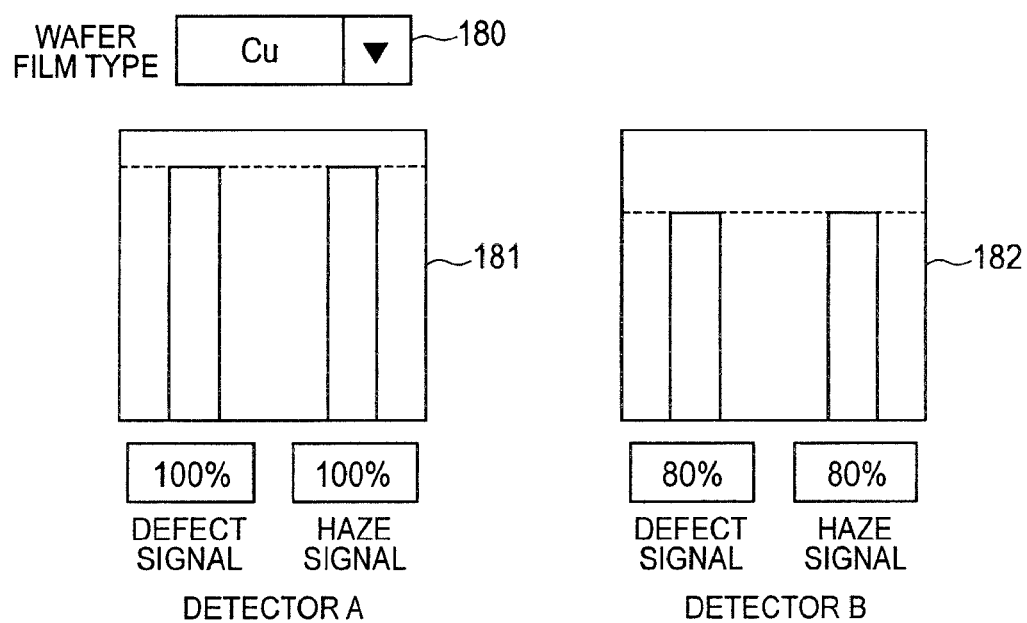
FIG. 18 illustrates an example user interface.

FIG. 18 exemplifies a user interface for the input portion 154. The user interface includes sub-windows 180, 181, and 182. The sub-window 180 specifies the type of a wafer to be inspected. The sub-windows 181 and 182 display rates of extracting or separating defect signals and haze signals on the detectors.

According to the invention, the optical detection system may be provided in multiple elevation angle directions and azimuth angle directions. Polarization states of the scattering light from a defect and that from a surface roughness vary with an elevation angle or an azimuth angle to be detected. The two scattering lights polarize in oscillation directions perpendicular to each other under some conditions. The two scattering lights polarize in approximately the same oscillation direction under other conditions.

Let us consider the detection system uses a detection condition that allows the defect scattering light and the surface roughness scattering light to have their polarization axes perpendicular to each other. In this case, the detection system can detect the defect scattering light and the surface roughness scattering light each with a purity of approximately 100% without attenuating them. Let us consider the detection system uses a detection condition that allows the defect scattering light and the surface roughness scattering light to have approximately the same polarization axis. In principle, the detection system can hardly separate the defect scattering light and the surface roughness scattering light from each other.

According to the above description, the azimuth angle and the elevation angle for detection almost uniquely determine the percentage of possibility of separating the defect scattering light and the roughness scattering light from each other. The polarization detection condition at that time can be almost uniquely determined. A simulation may be performed to previously calculate polarization states of the defect scattering light and the roughness scattering light corresponding to each detection azimuth angle and elevation angle for detection. A database may be used to store detection conditions for maximizing the rate of separation between the defect scattering light and the roughness scattering light. This makes it possible to easily generate a recipe and shorten the time to generate it.

The polarization state of the scattering light from a surface roughness varies with the material or surface roughness of a wafer to be inspected. A database may be used to store detection conditions for maximizing the rate of separation between the defect scattering light and the roughness scattering light in accordance with film types or surface roughnesses. This makes it possible to easily generate a recipe and shorten the time to generate it.

There may be a detection condition that makes the polarization separation difficult. Even in such a case, the signal processing portion may filter signals based on frequency bands and separately detect a high-frequency component as the defect detection signal and a low-frequency component as the haze detection signal.

The sub-window 180 enables selection of the film type to be inspected. For example, available film types include Si, Poly-Si, Cu, Al, W, and $SiO_2$ and are selectable from a pull-down menu. The operation specifies an initial value for the polarization detection condition of each detector. The initial value is reflected on display contents of the sub-windows 181 and 182.

As seen from the sub-windows 181 and 182 in FIG. 18, detector A can separate the defect scattering light and the roughness scattering light from each other at approximately 100% without attenuation due to the polarization detection. Detector B separates the defect scattering light and the roughness scattering light from each other at approximately 80% with approximately 20% attenuation due to the polarization detection.

The selection on the sub-window 180 specifies an initial value of the separation rate for the sub-windows 181 and 182. In addition, a user may specify the initial value. For example, the user may specify the separation rate of 80% for the defect scattering light on the sub-window 181 or the separation rate of 50% for the defect scattering light on the sub-window 182. In principle, however, the maximum separable rate is predetermined for each detection condition and is displayed as a dotted line in the sub-window. The separation rate cannot be specified over the maximum value.

The separation rate may be directly entered or may be selected from a pull-down menu.

According to the embodiment of the invention as described above, the polarization detection improves the defect detection sensitivity. In addition, the scattering light can be detected from a surface roughness without attenuation. The defect inspection and the haze measurement can be ensured at the same time. The invention may be embodied in other specific forms without departing from the spirit or essential characteristics thereof. The present embodiment is therefore to be considered in all respect as illustrative and not restrictive, the scope of the invention being indicated by the appended claims rather than by the foregoing description and all changes which come within the meaning and range of equivalency of the claims are therefore intended to be embraced therein.

The use of a laser beam with the wavelength band causing a large penetration depth can increase the irradiation energy and improve the detection sensitivity without damage to the wafer.

According to the embodiment of the invention, the photodiode array having multiple pixels is used to separate pixels into defect detection pixels and haze detection pixels. It is possible to improve the detection sensitivity based on the polarization and enable the haze measurement at the same time.

REFERENCE SIGNS LIST

1—Wafer
2, 2a, 2b—Laser light source
3, 3a, 3b—Beam expander
4, 4a, 4b—Polarization element
m—Mirror
6, 6a, 6b, 10a, 10b—Condensing lens
8—Detection lens
9—Beam splitter
11a, 11b, 74a, 74b, 75a, 75b—Filter
12a, 12b—Photomultiplier
20, 21—Polarization filter
25—Illumination spot
31—Penetration depth
32—Characteristics of the material having a small penetration depth
33—Characteristics of the material having a large penetration depth
34—Signal separator
35—Length of an illumination spot in the rotation direction
36—Timing to turn on or off the gate circuit of the defect signal detector
37—Timing to turn on or off the gate circuit of the haze signal detector
40—Imaging optical system
41, 72—Photodiode array
42—Condensing lens
43—Image intensifier
44—Imaging lens
50—Feeding pitch
60—Defect
61a . . . 61d—Pixels of the photodiode array
65—Memory
70a, 70b—Defect detection pixel
71a, 71b—Haze detection pixel
76—Memory for storing defect detection signals
77—Memory for storing haze detection signals
101, 101a, 101b—Illuminating optical system
102, 104a . . . 104f, 105—Optical detection system
102a—Defect optical detection system
102b—Haze optical detection system
103—Wafer stage
150—Analog circuit
151—Signal processing portion
152—CPU
153—Map output portion
154—Input portion
155—Stage control portion
160—Defect map
161—Haze map
170 . . . 174—Inspection flow
180 . . . 182—Sub-window
200, 200a, 200b—Laser beam
201—Normally reflected light
202—Transmitted light

The invention claimed is:

1. A defect inspecting method of inspecting a surface state including a defect on a wafer surface, the method comprises the steps of:
adjusting a polarization axis of a polarization filter;
irradiating a laser beam onto the wafer surface;
detecting a scattering light occurring from an irradiated region on the wafer surface via the adjusted polarization filter; and
separating a detected signal of the detected scattering light into a defect signal and a haze signal.

2. The defect inspecting method according to claim 1, wherein the polarization filter is configured to enable or disable a polarization axis rotation or filtering.

3. The defect inspecting method according to claim 1, wherein a polarization axis of the polarization filter is adjusted to a first polarization axis for defect measurement or a second polarization axis for haze measurement.

4. The defect inspecting method according to claim 1, wherein the polarization filter comprises segments each of which has an individual polarization axis.

5. The defect inspecting method according to claim 4, wherein the polarization axis varies one-dimensionally or two-dimensionally.

6. The defect inspecting method according to claim 1, wherein the detected scattering light is separated by a divider including one of amplitude division, wavelength division, and polarization division.

7. The defect inspecting method according to claim 1, wherein the laser beam is irradiated from a plurality of light sources having different wavelengths.

8. The defect inspecting method according to claim 1, wherein the laser beam is irradiated approximately vertically onto the wafer surface.

9. The defect inspecting method according to claim 1, wherein the laser beam is irradiated obliquely onto the wafer surface.

10. A defect inspecting apparatus for inspecting a surface state including a defect on a wafer surface, the apparatus comprising:
an irradiator which irradiates a laser beam onto the wafer surface;
a polarization filter;
a filter which adjusts a polarization axis of said polarization filter;
a detector which detects a scattering light occurring from an irradiated region on the wafer surface via the polarization filter; and
a separator which separates a detected signal the detected scattering light into a defect signal and a haze signal.

11. The defect inspecting apparatus according to claim 10, wherein the polarization filter is configured to enable or disable a polarization axis rotation or filtering.

12. The defect inspecting apparatus according to claim 11, wherein a polarization axis of the polarization filter is adjusted for defect measurement and for haze measurement.

13. The defect inspecting apparatus according to claim 11, wherein the polarization filter comprises segments each of which has an individual polarization axis.

14. The defect inspecting apparatus according to claim 13, wherein said polarization filter varies one-dimensionally or two-dimensionally.

15. The defect inspecting apparatus according to claim 11, further comprising a separator which separates the scattering light by a divider including one of amplitude division, wavelength division, and polarization division.

16. The defect inspecting apparatus according to claim 11, wherein the laser beam is irradiated from a plurality of light sources having different wavelengths.

17. The defect inspecting apparatus according to claim 10, wherein a polarization axis of the polarization filter is adjusted for defect measurement and for haze measurement.

18. The defect inspecting apparatus according to claim 10, wherein the laser beam is irradiated onto the wafer surface.

19. The defect inspecting apparatus according to claim 10, wherein a laser beam is irradiated obliquely onto the wafer surface.

* * * * *